(12) United States Patent
Baker

(10) Patent No.: US 6,594,021 B1
(45) Date of Patent: Jul. 15, 2003

(54) ANALYSIS SYSTEM FOR INTERFEROMETRIC SCANNING OF DONOR CORNEAL TISSUE

(75) Inventor: Phillip C. Baker, Orinda, CA (US)

(73) Assignee: Eyetech Vision, Inc., La Jolla, CA (US)

( * ) Notice: Subject to any disclaimer, the term of this patent is extended or adjusted under 35 U.S.C. 154(b) by 0 days.

(21) Appl. No.: 09/552,149

(22) Filed: Apr. 18, 2000

(51) Int. Cl.[7] .................................................. G01B 9/02
(52) U.S. Cl. ..................... 356/492; 356/432; 356/632; 356/440; 356/446; 351/212
(58) Field of Search ................... 356/492, 432, 356/433, 440, 446, 632; 351/212

(56) References Cited

U.S. PATENT DOCUMENTS

| | | | |
|---|---|---|---|
| 3,769,963 A | 11/1973 | Goldman et al. | |
| 4,019,813 A | * 4/1977 | Cornsweet et al. | ......... 348/135 |
| 4,091,814 A | 5/1978 | Togo | |
| 4,772,115 A | 9/1988 | Gersten et al. | |
| 4,781,453 A | 11/1988 | Kobayashi | |
| 5,062,702 A | 11/1991 | Bille | |
| 5,303,709 A | 4/1994 | Dreher | |

* cited by examiner

*Primary Examiner*—Robert H. Kim
*Assistant Examiner*—George Y Wang
(74) *Attorney, Agent, or Firm*—Nydegger & Associates

(57) ABSTRACT

A system for evaluating a donor cornea includes a light source for generating a beam having a predetermined characteristic and a selected configuration. The light beam characteristic can be collimated light (wavefront analysis), white light (spectral analysis), or polarized light (polarization analysis). The beam configuration can be either circular in cross-section, or it can be a slit. When circular, the light beam is transmitted through the entire cornea to identify changes in the characteristics of the light (e.g. phase shift, spectral shift, or polarization changes). These changes then determine the optical properties of the donor cornea. When configured as a slit, the light is scattered off-axis and used to measure dimensions for a profile of the donor cornea. A computer then prepares an evaluation which includes information on both the optical qualities and the dimensional profile of the donor specimen.

20 Claims, 1 Drawing Sheet

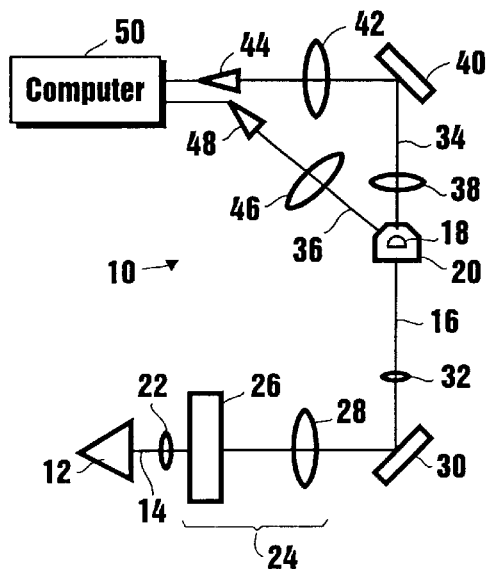
Figure 1
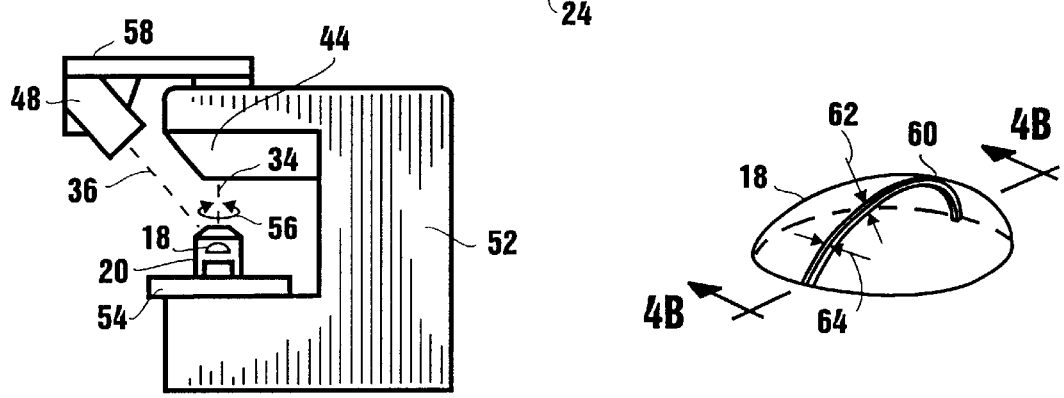
Figure 2
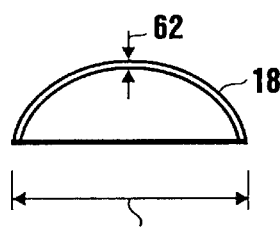
Figure 4A
Figure 4B
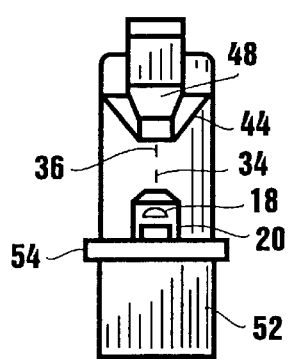
Figure 3A
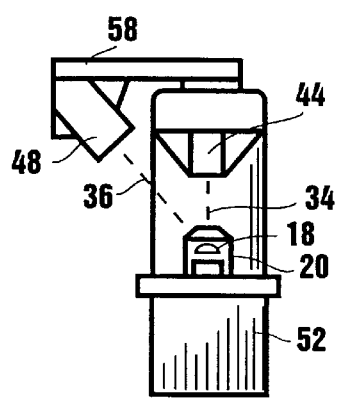
Figure 3B

ANALYSIS SYSTEM FOR INTERFEROMETRIC SCANNING OF DONOR CORNEAL TISSUE

FIELD OF THE INVENTION

The present invention pertains generally to devices and methods that are useful for inspecting and evaluating corneal donor tissue. More particularly, the present invention pertains to devices and methods that use optical techniques to evaluate both the material properties and the profile of corneal donor tissue in order to determine a composite optical structure of the donor cornea. The present invention is particularly, but not exclusively, useful for screening and selecting donor corneal tissue for the purpose of providing a suitable match for a particular transplant recipient.

BACKGROUND OF THE INVENTION

In order to determine whether a particular donor cornea is suitable for use in a transplant surgical procedure, there are essentially two issues which need to be addressed. The first concerns whether the donor cornea has the requisite optical properties for use in a transplant procedure. Obviously, if the donor cornea is incapable of achieving the desired optical performance, it should be rejected. The second issue, which is not so obvious, concerns whether an optically acceptable donor cornea has a physical profile that is suitable for use with a particular patient. The issues of optical quality and profile suitability are both important for the screening and selection of an appropriate donor cornea.

Insofar as the optical quality of a donor cornea is concerned, it is known that various optical interference techniques, such as interference polarization, wavefront analysis, or spectral analysis, can be useful for determining specific material properties of the cornea that will affect its optical quality. For example, it is known that optical interference techniques can be used to detect and identify inhomogeneities which may be caused by such tissue characteristics as density, amorphousness, crystallinity and transparency. Further, these interference techniques can also be used to detect residual tissue damage such as corneal scarring and stromal disease. Still further, they can be used to collect information concerning stress and anisotropy. As indicated above, a knowledge of these material properties of a donor cornea is of great importance to the vision healthcare provider. As also indicated above, however, for a more complete evaluation of a donor cornea it is also necessary to consider information about the physical profile of the donor cornea.

In addition to a thorough knowledge of the optical properties of a donor cornea, complete and accurate information on the dimensional profile of a donor cornea can be of great value to the healthcare professional who is performing a surgical transplant procedure. Not only does dimensional information permit a more suitable match between the donor and the recipient, it also allows for better control of tissue interface during surgery. Further, dimensional compatibility between donor and recipient can lead to a more effective surgical outcome with better patient response and shorter recovery time.

In light of the above it is an object of the present invention to provide a system and a method for evaluating a donor cornea which provides information concerning the optical properties of the cornea, as well as the physical profile of the cornea. It is another object of the present invention to provide a system and a method for evaluating a donor cornea which uses optical techniques to measure and evaluate both physical and optical properties of a donor cornea. Yet another object of the present invention is to provide a system and a method for evaluating a donor cornea which allows the donor cornea to remain inside the protective confines of a containment vessel during examination. Still another object of the present invention is to provide a system and a method for evaluating a donor cornea which is easy to use, relatively simple to implement, and comparatively cost effective.

SUMMARY OF THE PREFERRED EMBODIMENTS

A system for evaluating a donor cornea in accordance with the present invention includes a light source that will generate a light beam having a predetermined characteristic and a selected configuration. Specifically, insofar as the light beam characteristics are concerned, the light from the light source can be collimated light for use in a wavefront analysis, it can be white light for use in a spectral analysis, or it can be polarized light for use in a polarization analysis. Insofar as light beam configurations are concerned, the light beam can have a generally circular cross-section so that the light will simultaneously illuminate an entire donor cornea, or it can have a slit configuration so that only a relatively narrow strip of the donor cornea will be illuminated.

As intended for the device of the present invention, when the light beam is in its circular cross-section configuration, the light is directed along a path through the donor cornea to a detector. More specifically, this path will be generally aligned with the optical axis of the donor cornea. For a circular cross-section light beam configuration, the entire donor cornea will be illuminated. The detector can then evaluate the light that is transmitted through the donor cornea, including the endothelium, to identify changes in the characteristics of the light (e.g. phase shift, spectral shift, or polarization changes). In turn, these changes can be used to evaluate the optical aberrations that are introduced by the donor cornea. Based on this evaluation, the optical properties of the donor cornea are determined in a manner well known in the art.

Regardless of the particular characteristics chosen for the light beam that is used to determine the optical properties of the donor cornea, when the light beam is switched to its slit configuration, some of the light will be scattered off-axis by the donor cornea. This scattered light can then be collected by another detector and used to measure dimensions for a profile of the donor cornea. For example, these dimensions can include a thickness, an arc length, and a chord length for the donor cornea.

In addition to the optical elements for the present invention set forth above, the device of the present invention can also include a cell for holding the donor cornea. An example of such a cell is disclosed in co-pending U.S. patent application Ser. No. 09/464,110, for an invention entitled "Optical Donor Tissue Cell", which is assigned to the same assignee as the present invention. The present device can also include a mount that has a stage for holding the cell. Additionally, the cell can be rotated with the stage to move the donor cornea relative to the light source, or the scattered light detector can be moved relative to the donor cornea in the cell. Either way, different slits of the donor cornea can be illuminated for subsequent analysis and use in establishing a profile for the donor cornea.

In the operation of the present invention, the light beam from the light source is directed along an initial path toward the donor cornea. Before the light beam reaches the donor cornea, the particular desired characteristic for the light beam is established. Specifically, the light can be collimated, polarized, sheared or otherwise defined. Additionally, a switching means is provided for selectively alternating the light beam between its first configuration, wherein the light beam is dimensioned to illuminate the entire cornea, and its second configuration wherein the light beam is dimensioned to illuminate only a slit of the donor cornea.

When the light beam is in its first configuration to illuminate the entire cornea, the light that is transmitted through the donor cornea is evaluated to determine the optical characteristics of the donor cornea. Depending on the characteristic of the light beam, this evaluation can be done either by wavefront analysis, spectral analysis, or polarization analysis to provide information on such material qualities of the donor cornea as tissue strain, tissue stress, temperature degradation, extracorporeal aging, and damage. When the light beam is in its second configuration, for slit illumination of the donor cornea, scattered light from the illuminated slit can be used to determine anterior and posterior edges of the corneal specimen (donor cornea). Also, radii of curvature information and elevation data, as well as corneal thickness and chord length can be determined.

A computer for collating data collected by the detectors is then used to prepare an evaluation report of the donor cornea. As specifically intended for the present invention, this evaluation report will include information on both the optical qualities and the dimensional profile of the donor specimen. Accordingly, the evaluation report is useful for screening and selecting an appropriate specimen for a recipient, and for use in planning a surgical transplant procedure.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a schematic of the optical paths used by the present invention for the evaluation of a donor cornea;

FIG. 2 is a side elevation view of the device of the present invention;

FIG. 3A is a front elevational view of the device of the present invention in a first orientation;

FIG. 3B is a front elevational view of the device of the present invention in a second orientation;

FIG. 4A is a perspective view of a donor cornea during regional illumination of a slit of the cornea; and FIG. 4B is a cross-sectional view of the donor cornea as seen along the line 4B—4B in FIG. 4A.

DESCRIPTION OF THE PREFERRED EMBODIMENT

Referring initially to FIG. 1, a schematic of an optical system for evaluating a donor cornea in accordance with the present invention is shown and generally designated 10. As shown, the system 10 includes a light source 12 for generating a light beam 14 that is directed along an initial path 16 to illuminate a donor cornea 18. For the present invention, the donor cornea 18 is preferably held in a cell (containment vessel) 20 that is of a type as disclosed and claimed in co-pending U.S. patent application Ser. No. 09/464,110, which is assigned to the same assignee as the present invention.

In more detail, the system 10 includes a focusing lens 22 which focuses the light beam 14. The system 10 also includes a transmission unit 24 which can be used to characterize the light beam 14. Depending on the characteristic that is established for the light beam 14, a particular optical analysis technique can be used to evaluate the optical properties of the donor cornea 18.

For one embodiment of the present invention, the transmission unit 24 can include a shear waveplate 26 and a collimating lens 28. For this embodiment of the system 10, the transmission unit 24 establishes a characteristic for the light beam 14 that is phase referenced. Specifically, as is known in the pertinent art, by establishing a phase reference for the light beam 14, phase changes that are caused by optical aberrations in the donor cornea 18 (including the endothelium) can be subsequently evaluated using wavefront analysis techniques. For example, the light beam 14 can be characterized by an initial wavefront before passing through the donor cornea 18. As the initial wavefront passes through the donor cornea 18, however, it will be distorted by any optical aberrations that may be present. Differences between the initial wavefront and the distorted wavefront can then be used, in a manner well known to the skilled artisan, to determine the optical quality of the donor cornea 18. With a wavefront analysis, both phase analysis and fringe analysis determinations may be involved.

In another embodiment of the system 10, the transmission unit 24 can be a light polarizer. In this case, a polarization reference can be established for the light beam 14, and polarization changes that are caused by optical aberrations in the donor cornea 18 can be subsequently evaluated using polarization analysis techniques to determine the optical quality of the donor cornea 18 (including the endothelium).

In yet another embodiment of the system 10, the transmission unit 24 can be effectively eliminated and the light source 12 can be caused to generate a white light. When white light is used, spectral analysis techniques that are well known in the art can be used to analyze optical aberrations introduced by the donor cornea 18. More specifically, the color spectral response which results when white light passes through the donor cornea 18 will be a spectral shift that is indicated of the optical quality of the donor cornea 18.

Importantly, when using the various techniques discussed above, many material and optical qualities of the donor cornea 18 may be determined. For example, the condition of the endothelium can be assessed, as well as the condition of stromal layers in the donor cornea 18. As intended for the present invention, one or more of the optical techniques mentioned herein can be used individually or in combination to obtain the particularly desired data for evaluation of the optical quality of the donor cornea 18.

After the characteristic of light beam 14 has been established (e.g. collimated light, polarized light, or white light) the light beam 14 is directed toward a folding (turning) mirror 30 and along the initial path 16 toward the donor cornea 18 inside containment vessel 20. Before reaching the containment vessel 20, however, light beam 14 encounters a slit 32. As intended for the present invention, the slit 32 can be selectively activated to establish alternative configurations for the light beam 14. In one configuration, the slit 32 is deactivated so that it has no effective influence on the light beam 14. In this case, the light beam 14 continues along the initial path 16 toward the donor cornea 18 and containment vessel 20 with a substantially circular cross-section. In this configuration, the light beam 14 illuminates the entire donor cornea 18, and an analysis as discussed above is accomplished. In another configuration, the slit 32 is activated so that only a slit of light will illuminate a region of the donor cornea 18.

In either configuration (i.e. circular cross-section, or slit), the light beam 14 is directed from folding mirror 30 toward the donor cornea 18 along the initial path 16. Preferably, initial path 16 is substantially coaxial with the optical axis of the donor cornea 18. Depending on the configuration of light beam 14, however, once the light beam 14 has illuminated the donor cornea 18, it will take either of two different paths. When light beam 14 is in the circular cross-section configuration, it illuminates the entire donor cornea 18 and is transmitted along the direct path 34. Specifically, the direct path 34 is substantially coaxial with the initial path 16. As indicated above, any or all of several optical techniques can then be used for analyzing the donor cornea 18. On the other hand, when light beam 14 is in the slit configuration, it illuminates only a slit 32 of the donor cornea 18 and light is scattered off-axis along a deflected path 36. As intended for the present invention, the deflected path 36 can be at an angle in the range between approximately fifteen degrees and fifty degrees (15°–50°).

When light beam 14 is in the circular cross-section configuration, and is directed as transmitted light along the direct path 34, it may pass through a scatterplate screen 38, if necessary. In any event, the transmitted light will be reflected by folding (turning) mirror 40 and directed through a telecentric lens unit 42 to a detector 44. On the other hand, when light beam 14 is in the slit configuration, it will be directed as scattered light along the deflected path 36. The scattered light will then be directed through a telecentric lens unit 46 to a detector 48. As shown in FIG. 1, both the detectors 44 and 48 are connected with a computer 50 which will receive signals from the respective detectors 44, 48 for analysis.

As indicated in FIG. 2, all of the components of the system 10 described above can be effectively positioned in a housing 52. Further, the housing 52 can have a mount 54 on which the containment vessel 20 and donor cornea 18 can be positioned. For one mode of operation for the system 10, the mount 54 can be rotated by a motor (not shown). Specifically, in this mode of operation, both the mount 54 and containment vessel 20 are rotated in directions indicated by the arrow 56 through a plurality of stages on the housing 52. This can be accomplished while the housing 52 remains substantially fixed (cross reference FIG. 2 with FIG. 3A). In another mode of operation, the containment vessel 20 can be held stationary on the mount 54 and housing 52, while the gantry 58 is rotated (cross reference FIG. 3A with FIG. 3B). In either case, the result is that the detector 48 can view a plurality of different illuminated slits 60 of the donor cornea 18.

In FIG. 4A, an exemplary slit 60 in the donor cornea 18 is shown. As shown in FIG. 4A and FIG. 4B, the slit 60 has a thickness 62, a width 64 and a length 66. Importantly, when the light beam 14 is configured in its slit configuration, a slit 60 will be illuminated. Scattered light from the slit 60 will then be sent along the deflected path 36 for receipt by the detector 48.

In the operation of the system 10 of the present invention, a donor cornea 18 is positioned inside a containment vessel (cell) 20 where it is suspended in a medium, such as a saline solution, a transmissive gel or plastic, glass or some other hydrogel media. Light source 12 is then activated to illuminate the donor cell 18. Specifically, at this point the light beam 14 that is generated by the light source 12 can be established to have a particular characteristic (e.g. collimated light, polarized light, or white light). Also the light beam 14 can be formed to have a particular configuration. With the slit 32 disengaged or inactivated, the light beam 14 will have a substantially circular cross-section configuration and will illuminate the entire donor cornea 18. Light transmitted through the donor cornea 18 will then be directed along the direct path 34 to the detector 44. On the other hand, when the slit 32 is engaged or activated, the light beam 14 will have a slit configuration and only a regional slit 60 of the donor cornea 18 will be illuminated. Light scattered from the slit 60 will then be directed along the deflected path 36 to the detector 48. Signals from the detectors 44 and 48 are then used by the computer 50 for analyzing the donor cornea 18.

While the particular Analysis and System for Interferometric Scanning of Donor Corneal Tissue as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for evaluating a donor cornea which comprises:

a light source for generating a light beam having a predetermined characteristic;

an optical means for directing said light beam along an initial path toward said donor cornea;

a switching means for selectively alternating said light beam between a first configuration wherein said light beam is dimensioned to illuminate said entire cornea and a second configuration wherein said light beam is dimensioned to illuminate a slit of said donor cornea;

a first detector for collecting data in light transmitted through said donor cornea onto a first optical path when said light beam is in said first configuration wherein said first optical path is a coaxial extension of the initial path;

a second detector for collecting data in light scattered by said donor cornea onto a second optical path when said light beam is in said second configuration; and a computer means for collating data collected by said first and second detectors to prepare an evaluation report documenting tissue characteristics of said donor cornea.

2. A system as recited in claim 1 wherein said first optical path is coaxial with said initial path and said second optical path is oriented at an angle to said initial path.

3. A system as recited in claim 1 wherein said light beam has an initial wavefront, wherein said predetermined characteristic is collimation, and wherein said transmitted light has a distorted wavefront caused by aberrations in said donor cornea, with said data in said transmitted light being differences between said initial wavefront and said distorted wavefront indicative of said tissue characteristics.

4. A system as recited in claim 1 wherein said predetermined characteristic of said light beam is white light, and wherein said transmitted light is distorted by aberrations in said donor cornea, with said data in said transmitted light being a color spectral response exhibiting a spectral shift indicative of said tissue characteristics.

5. A system as recited in claim 1 wherein said predetermined characteristic of said light beam is polarization, and wherein said transmitted light is distorted by aberrations in said donor cornea, with said data in said transmitted light being variations in polarization indicative of said tissue characteristics.

6. A system as recited in claim 1 wherein said slit has dimensions for illuminating said donor cornea to determine a thickness, an arc length, and a chord length for the donor cornea.

7. A system as recited in claim 1 wherein said tissue characteristics include, tissue strain, tissue stress, temperature degradation, extracorporeal aging, and damage.

8. A system as recited in claim 1 further comprising:
   a cell for holding said donor cornea;
   a mount having a stage for holding said cell; and
   a motor means for rotating said mount to rotate said donor cornea relative to said light source through a plurality of stages for illuminating a plurality of different said slits for collection by said second detector.

9. A system for evaluating a donor cornea which comprises:
   a cell for holding said donor cornea;
   a means for directing a light beam on an initial path to pass through said donor cornea to generate a beam of transmitted light passing along a first optical path, wherein said first optical path is a coaxial extension of the initial path, and a beam of scattered light passing along a second optical path;
   a detector assembly for collecting said transmitted light and said scattered light to retrieve data contained therein; and
   a computer means for collating data collected by said detector assembly to prepare an evaluation report documenting tissue characteristics of said donor cornea.

10. A system as recited in claim 9 wherein said detector assembly comprises:
    a first detector positioned on said first optical path for collecting said transmitted light; and
    a second detector positioned on said second optical path for collecting said scattered light.

11. A system as recited in claim 10 further comprising a switching means for selectively alternating said light beam between a first configuration wherein said light beam is dimensioned to illuminate said entire cornea and a second configuration wherein said light beam is dimensioned to illuminate a slit of said donor cornea.

12. A system as recited in claim 11 wherein said light beam has an initial wavefront, and wherein said transmitted light has a distorted wavefront caused by aberrations in said donor cornea, with said data in said transmitted light being differences between said initial wavefront and said distorted wavefront indicative of said tissue characteristics.

13. A system as recited in claim 11 wherein said light beam is white light, and wherein said transmitted light is distorted by aberrations in said donor cornea, with said data in said transmitted light being a color spectral response exhibiting a spectral shift indicative of said tissue characteristics.

14. A system as recited in claim 11 wherein light in said light beam is polarized, and wherein said transmitted light is distorted by aberrations in said donor cornea, with said data in said transmitted light being variations in polarization indicative of said tissue characteristics.

15. A system as recited in claim 11 wherein said slit has dimensions for illuminating said donor cornea to determine a thickness, an arc length, and a chord length for the donor cornea.

16. A system as recited in claim 11 wherein said tissue characteristics include, tissue strain, tissue stress, temperature degradation, extracorporeal aging, and damage.

17. A method for evaluating a donor cornea which comprises the steps of:
    generating a light beam having a predetermined characteristic;
    directing said light beam along an initial path toward said donor cornea;
    selectively alternating said light beam between a first configuration wherein said light beam is dimensioned to illuminate said entire cornea and a second configuration wherein said light beam is dimensioned to illuminate a slit of said donor cornea;
    collecting data in light transmitted through said donor cornea onto a first optical path, wherein said first optical path is a coaxial extension of the initial path, when said light beam is in said first configuration, and data in light scattered by said donor cornea onto a second optical path when said light beam is in said second configuration; and
    collating said collected data to prepare an evaluation report documenting tissue characteristics of said donor cornea.

18. A method as recited in claim 17 further comprising the steps of:
    holding said donor cornea in a cell;
    placing said cell on a mount; and
    rotating said mount to rotate said donor cornea relative to said light source through a plurality of stages for illuminating a plurality of different said slits for respective collection as scattered light.

19. A method as recited in claim 17 wherein said slit has dimensions for illuminating said donor cornea to determine a thickness, an arc length, and a chord length for the donor cornea.

20. A method as recited in claim 17 wherein said tissue characteristics include, tissue strain, tissue stress, temperature degradation, extracorporeal aging, and damage.

* * * * *